(12) United States Patent
Dericco

(10) Patent No.: US 10,245,121 B2
(45) Date of Patent: Apr. 2, 2019

(54) TOOTHBRUSH

(71) Applicant: Salvatore P. Dericco, W. Harrison, NY (US)

(72) Inventor: Salvatore P. Dericco, W. Harrison, NY (US)

( * ) Notice: Subject to any disclaimer, the term of this patent is extended or adjusted under 35 U.S.C. 154(b) by 0 days.

(21) Appl. No.: 15/682,017

(22) Filed: Aug. 21, 2017

(65) Prior Publication Data

US 2018/0049844 A1    Feb. 22, 2018

Related U.S. Application Data

(60) Provisional application No. 62/377,356, filed on Aug. 19, 2016.

(51) Int. Cl.

| | |
|---|---|
| *A46B 5/02* | (2006.01) |
| *A61C 3/00* | (2006.01) |
| *A46B 5/00* | (2006.01) |
| *A61D 5/00* | (2006.01) |
| *A46B 9/04* | (2006.01) |

(52) U.S. Cl.
CPC .............. *A61C 3/005* (2013.01); *A46B 5/0016* (2013.01); *A46B 9/04* (2013.01); *A46B 2200/10* (2013.01); *A46B 2200/1066* (2013.01); *A46B 2200/1086* (2013.01); *A61D 5/00* (2013.01)

(58) Field of Classification Search
CPC .......... A46B 5/0004; A46B 2200/1093; A46B 2200/1086; A46B 5/0016

USPC ................................................ 15/167.1, 105
See application file for complete search history.

(56) References Cited

U.S. PATENT DOCUMENTS

| | | | | |
|---|---|---|---|---|
| D160,919 S | * | 11/1950 | Brooks | .......................... D4/105 |
| 2,668,308 A | * | 2/1954 | Grossman | ................ A46B 9/04 |
| | | | | 15/106 |
| 2,991,494 A | * | 7/1961 | Smith | ..................... A47L 17/00 |
| | | | | 15/106 |
| D279,049 S | * | 6/1985 | Putkonen | ........................ 15/106 |
| 4,679,273 A | | 7/1987 | Okin | |
| 4,738,001 A | * | 4/1988 | Shipp | ..................... A01K 13/00 |
| | | | | 15/106 |
| 5,383,244 A | * | 1/1995 | Ahrens | ................ A46B 5/0008 |
| | | | | 15/106 |
| 5,758,380 A | * | 6/1998 | Vrignaud | ............. A46B 5/0012 |
| | | | | 15/106 |
| D490,984 S | * | 6/2004 | Wong | ............................. D4/105 |
| D658,888 S | * | 5/2012 | Prochaska | ..................... D4/105 |
| 2012/0055497 A1 | * | 3/2012 | Hurwitz | ................... A46B 9/04 |
| | | | | 132/200 |
| 2013/0276253 A1 | * | 10/2013 | Chen | ........................ A46B 9/04 |
| | | | | 15/106 |

* cited by examiner

*Primary Examiner* — Michael D Jennings
(74) *Attorney, Agent, or Firm* — Maier & Maier, PLLC

(57) ABSTRACT

According to an exemplary embodiment, a toothbrush having one or two heads for use in a variety of humans and animals may be shown and described. The toothbrush can have offset heads and bristle areas, include multiple curves of an arm portion to provide improved access and cleaning ability, and may be separable or combined with other toothbrush elements or components.

20 Claims, 11 Drawing Sheets

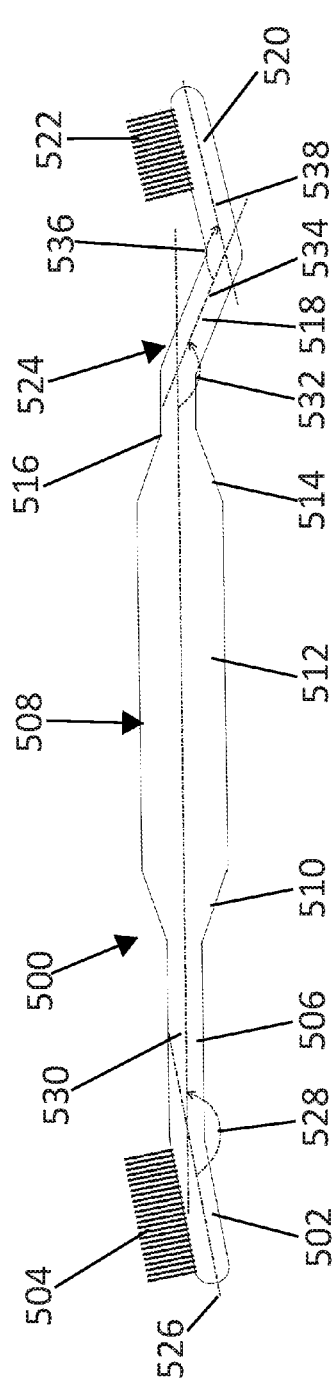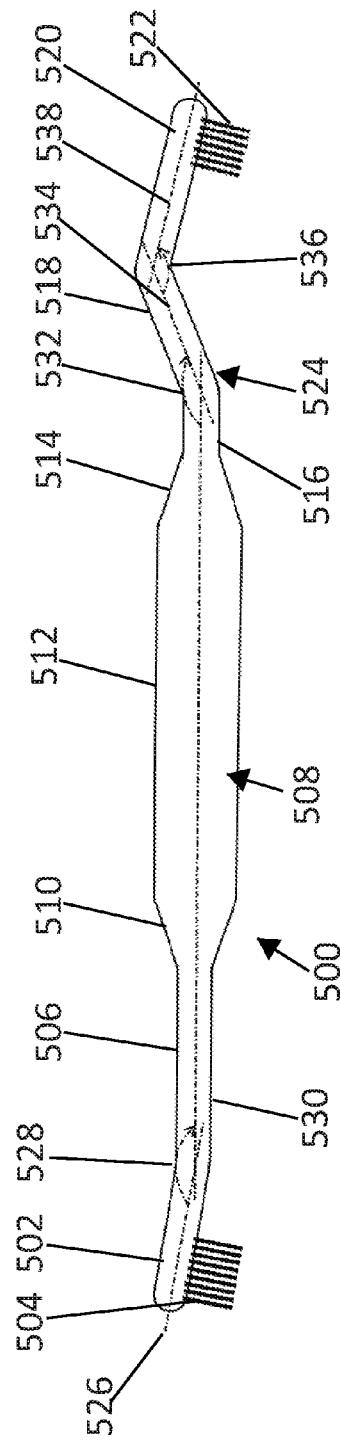
FIG. 10
FIG. 11

TOOTHBRUSH

CROSS-REFERENCE TO RELATED APPLICATIONS

This application claims priority from U.S. Provisional Patent Application No. 62/377,356, filed on Aug. 19, 2016, entitled "TOOTHBRUSH," the entire contents of which are hereby incorporated by reference.

BACKGROUND

Humans and animals alike need to maintain oral hygiene. Animals, namely domesticated animals and pets, routinely suffer from various oral hygiene issues due to genetics, diet, living conditions, or any combination of the three. Cats and dogs are typically treated by a veterinarian for various oral hygiene issues, but owners typically have little tendency to assist with oral hygiene issues.

Presently available toothbrushes are typically designed for humans, and/or are not well proportioned or otherwise suited for use in pets, such as cats, dogs, or other domesticated animals. The brushes are often too large, have too many bristles, have excessively stiff bristles, or do not provide proper articulation to function in the mouth of an animal.

Additionally, due to the use of various orthodontics and natural variations in the jaw and tooth orientation of humans, known toothbrushes do not provide effective cleaning capabilities to provide desired oral hygiene. Certain devices, such as orthodontic braces, can contribute to plaque buildup by trapping food in and around the braces, which allows dental plaque to easily accumulate. Conventional toothbrushes are not adapted to properly clean all areas of the teeth of a user with braces, and in particular have trouble reaching and cleaning regions of the teeth between the brackets and gum line or gingival region, in large part because the brackets themselves obstruct this region. The heads of conventional toothbrushes are also not adapted to adequately and comfortably fit into the oral vestibule in order to access these areas if the toothbrush needs to bypass orthodontic appliances.

SUMMARY

A toothbrush having one or two heads for use in a variety of humans and animals may be shown and described. The toothbrush can have offset heads and bristle areas, include multiple curves of an arm portion to provide improved access and cleaning ability, and may be separable or combined with other toothbrush elements or components.

For example, a brush may be provided having a brush head having a base that is offset and disposed at an angle with respect to the handle. In some exemplary embodiments, the brush may be provided with two brush heads, one located on either side of the brush, and each of the brush heads being disposed at an angle relative to the handle. This angle may be used in order to provide a toothbrush having a brush head that is disposed in an optimal position with respect to the gingival regions of the teeth of a human or animal, including a human having orthodontic appliances installed in his or her mouth.

The handle of the toothbrush may have planar surfaces and a square cross section, or may have another shape such as a cylindrical shape with a circular cross section.

A toothbrush may also be provided having bristle tufts that extend from the base of a brush head at an oblique angle with respect to a planar surface of the handle. The tufts may be provided on a thin brush head, such as a small, cylindrical brush head, which may have a single row of bristle tufts disposed in a row on the brush head. The tufts may also be provided such that a plurality of rows are provided in a parallel or staggered arrangement.

According to an exemplary embodiment, a toothbrush for cleaning gums and teeth in the mouth of a human or animal may be provided. Such a toothbrush may include a handle having a proximal end and a distal end, with a first arm disposed on the proximal end of the handle and a second arm disposed on the distal end of the handle, each arm being coplanar with a longitudinal plane of the handle (such that the brush can be laid flat in a direction perpendicular to the direction of extent of the handle and direction of orientation of the bristles), each arm extending outward from the handle in an initial direction collinear with a longitudinal axis of the handle. The second arm may include at least one bent portion, the at least one bent portion of the second arm extending laterally in a first lateral direction from the longitudinal axis of the handle at a second arm first angle. The toothbrush may further include a first brush head and a second brush head, each brush head being coplanar with the longitudinal plane of the handle, the first brush head extending laterally from the longitudinal axis of the handle at a first arm angle and the second brush head extending laterally from the at least one bent portion of the second arm at a second arm second angle, wherein the second brush head extends in a second lateral direction opposite the first lateral direction, such that the combination of the second arm and second brush head has a hook-shape. The toothbrush may further include at least one bristle tuft extending laterally from each of the first brush head and the second brush head, each bristle tuft being oriented perpendicular to a longitudinal axis of the brush head.

In some exemplary embodiments, the first arm angle of the toothbrush may be an angle between 9 and 50 degrees, for example 10 degrees. In some exemplary embodiments, the second arm first angle may be an angle between 20 and 50 degrees, for example 23 degrees. In some exemplary embodiments, the second arm second angle may be an angle between 20 and 120 degrees, for example 36 degrees; an oblique angle may be formed between the second brush head and the handle. Other angle measurements in these ranges may also be contemplated; for example, in an exemplary embodiment, a first arm angle may be provided at 20 degrees, a second arm first angle may be provided at 30 degrees, and a second arm second angle may be provided at 90 degrees. (In some exemplary embodiments, such as in exemplary embodiments where a second arm second angle or other angle is particularly large, it may be desired to separate the arm into multiple components, which may, for example, be joined at a position coinciding with the placement of the angle.) In some exemplary embodiments, the at least one bristle tufts disposed on each brush head may be disposed on identical sides of the toothbrush. In some exemplary embodiments, the handle of the toothbrush may have a polygonal cross-section and may be linear, and each of the first arm, the second arm, the first brush head, and the second brush head may have a cylindrical shape with a circular cross-section, each of the first brush head and the second brush head may have a dome-shaped end; the handle may have a thickness greater than the thickness of the first arm and the second arm; and the proximal end and the distal end of the handle may taper from the handle to the first arm and the second arm. In some exemplary embodiments, the bristle tufts may extend between 5 and 10 mm from the brush head, for example 8 mm from the brush head. In some exemplary embodiments, the bristle tufts may be arranged in a line, or may be arranged in another configuration such as may be desired. In some exemplary embodiments, the handle may be formed from multiple pieces, such as a proximal end piece and a distal end piece, which may be mated at a connector; in some exemplary embodiments, the pieces may be decoupled from one another, and in some exemplary embodiments the pieces may be used to adjust the relative orientations of the brush heads by rotating the pieces at the connector.

According to another exemplary embodiment, a toothbrush for cleaning gums and teeth in the mouth of a human or animal may be provided, which may have a handle having a proximal end and a distal end; an arm disposed on the distal end of the handle, said arm having a cylindrical shape and substantially circular cross section, the arm being coplanar with a longitudinal plane of the handle, the arm extending outward from the handle in an initial direction collinear with a longitudinal axis of the handle; a brush head, the brush head being coplanar with the longitudinal plane of the handle, the brush head extending laterally from the longitudinal axis of the handle at an angle in a first lateral direction, said brush head having a substantially circular cross-section and a substantially dome-shaped end; at least one bristle tuft extending laterally from the brush head, the at least one bristle tuft being oriented perpendicular to a longitudinal axis of the brush head, the at least one bristle tuft having a plurality of bristles having a length of between 5 mm and 10 mm and extending from the brush head in a common direction and parallel with each other; and a connector disposed on the proximal end of the handle, the connector configured to couple the toothbrush to a second toothbrush to form a double-ended toothbrush. In some exemplary embodiments, this may allow a portion of a double-ended toothbrush having a first arm and a portion of a double-ended toothbrush having a second arm to function as separated toothbrushes, should this be desired.

According to another exemplary embodiment, a toothbrush for cleaning gums and teeth in the mouth of a human or animal may be provided, and may include a handle having a proximal end and a distal end; an arm disposed on the distal end of the handle, said arm having a cylindrical shape and substantially circular cross section, the arm being coplanar with a longitudinal plane of the handle, the arm extending outward from the handle in an initial direction collinear with a longitudinal axis of the handle; a brush head, the brush head being coplanar with the longitudinal plane of the handle, the brush head extending laterally from the longitudinal axis of the handle at an angle in a first lateral direction, said brush head having a substantially circular cross-section and a substantially dome-shaped end; and at least one bristle tuft extending laterally from the brush head, the at least one bristle tuft being oriented perpendicular to a longitudinal axis of the brush head, the at least one bristle tuft comprising a plurality of bristles having a length of between 5 mm and 10 mm and extending from the brush head in a common direction and parallel with each other. The handle may include a gripping portion disposed on a proximal end of the handle and having a polygonal cross-section, a neck portion thinner than the gripping portion disposed on a distal side of the gripping portion and having a circular cross-section, and a handle node portion thicker than the neck portion and disposed on a distal side of the neck portion, the neck tapering from a thicker proximal side to a thinner distal side.

In some exemplary embodiments, the brush head may extend laterally at an angle of between 9 and 40 degrees. In some exemplary embodiments, the brush head may have a plurality of bristle tufts, which may be arranged in a line on the bristle head or may be provided in another arrangement as may be desired. In some exemplary embodiments, the handle node portion may have a polygonal cross section and may taper from the thicker proximal side to the thinner distal side, the thinner distal side having the arm disposed thereon.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 10 is an exemplary image of a double headed toothbrush with varying arm contours.

FIG. 11 is an exemplary image of a double headed toothbrush with varying arm contours.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Generally referring to the figures, a method, system and apparatus for a toothbrush may be shown and described. The toothbrush can be formed in a variety of designs and utilize various combinations of heads, arms, and bristles to provide desired oral hygiene capabilities.

Figure 1:
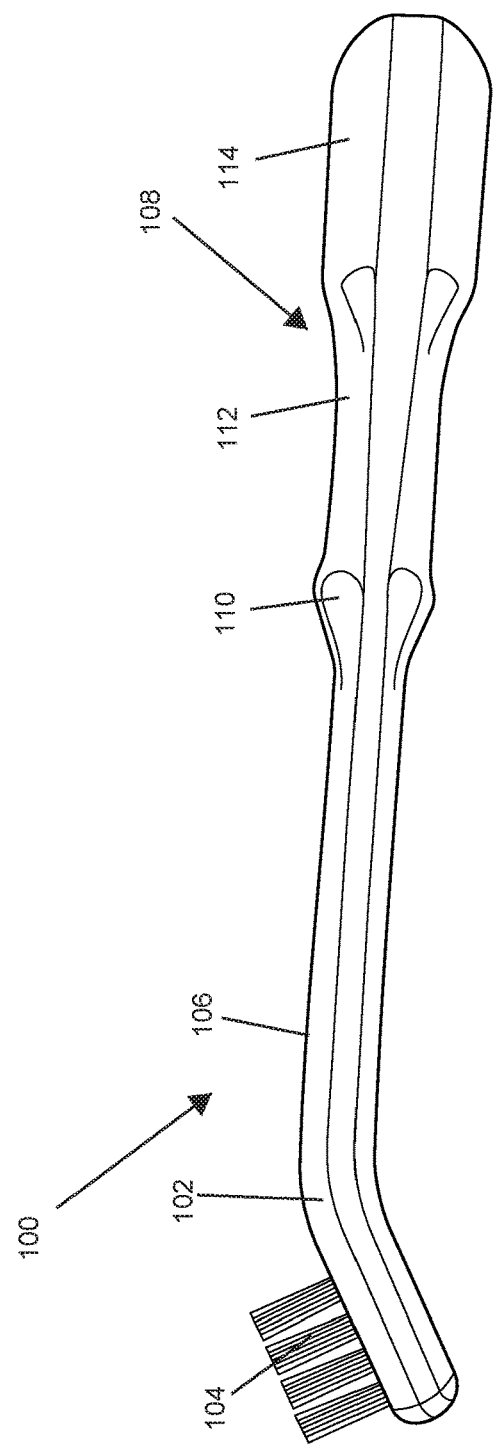
FIG. 1 is an exemplary perspective image of a toothbrush.
Figure 2:
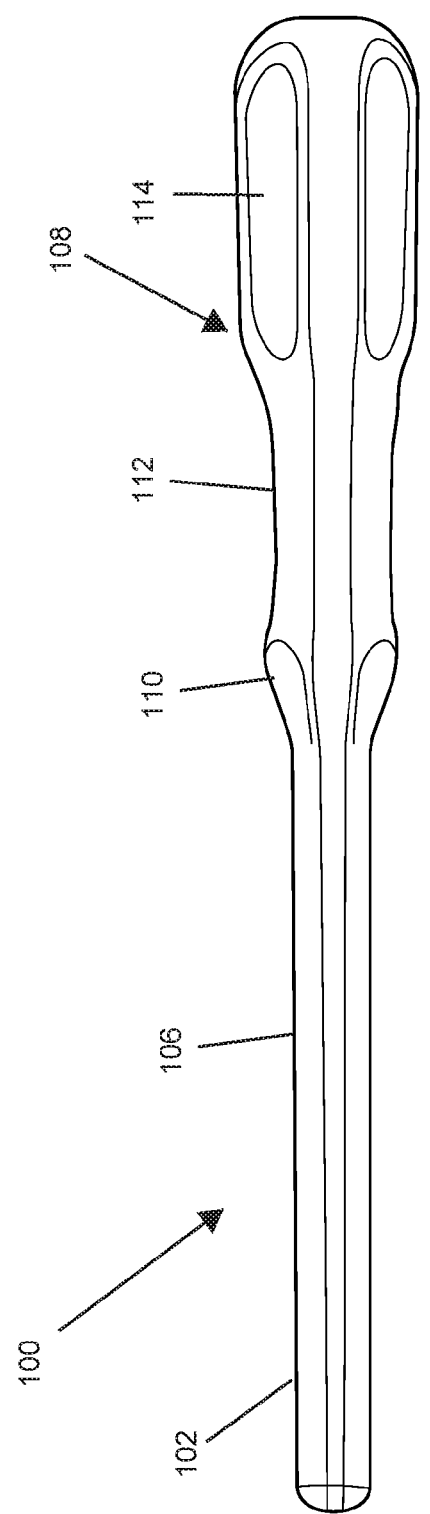
FIG. 2 is an exemplary rear image of a toothbrush.
Figure 3:
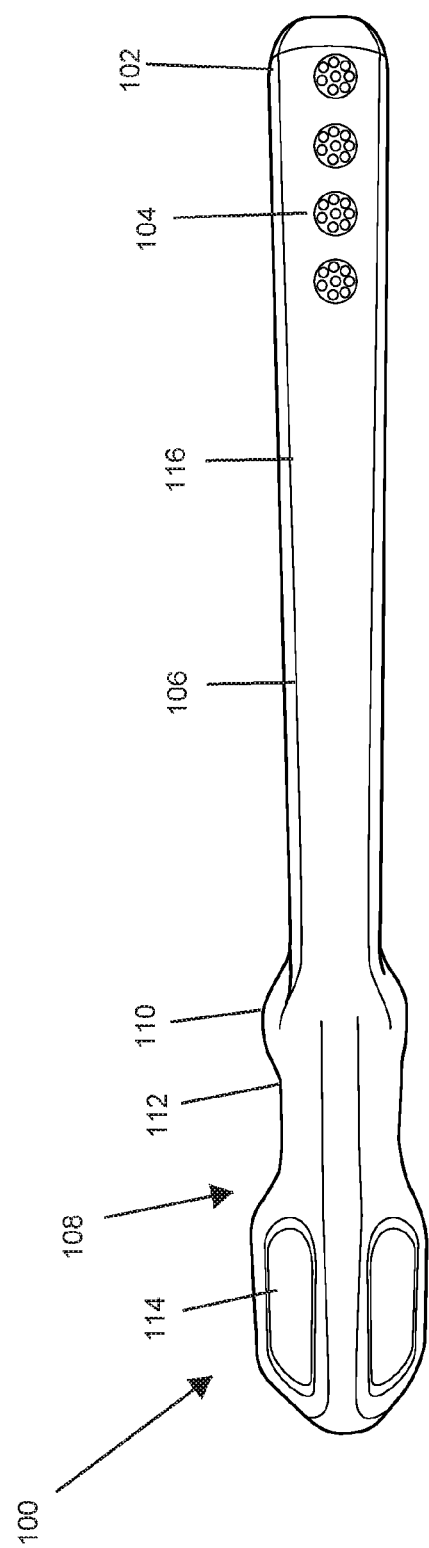
FIG. 3 is an exemplary top down image of a toothbrush.

Referring now to exemplary FIGS. 1-3, a toothbrush or a head, arm, and handle portion of a toothbrush may be shown. The toothbrush may be formed out of any of a variety of materials, including, but not limited to, plastics, composites, or any other desired material. The toothbrush can have a handle formed as a body and a gripping portion, an arm portion, and a head portion. The arm and/or head portion may be substantially curved, as desired, and as shown in exemplary FIG. 1. Further, the head may include a plurality of bristle tufts. The bristle tufts may be utilized in any number, for example four bristle tufts, and may be spaced apart substantially equidistantly. It may further be appreciated that the number of bristle tufts may be from three to eight tufts, as desired and depending on the intended use of the brush; for example, the number of bristle tufts may be varied based on what species the toothbrush is intended to be used on. The spacing between bristle tufts may vary between brushes; for example, according to some exemplary embodiments, bristle tufts may be spaced apart at a distance of about 0.5 mm to about 4 mm, or may be spaced apart at a different distance, if desired. The length of the brushes may vary on a brush or between brushes; for example, in some exemplary embodiments, the bristles may have lengths of 5 mm to about 10 mm or more, as desired. The total length of the head of the toothbrush may also vary between exemplary embodiments of the toothbrush; for example, in some exemplary embodiments, the total length of the head of the toothbrush may vary from about 6 mm to about 20 mm or more, as desired. Likewise, the total length of other components of the toothbrush, such as the handle or the arm of the toothbrush, may also vary between exemplary embodiments of the toothbrush, such as may be desired. (Variance of the total length of any component or any combination of components of the toothbrush may be understood for any of the exemplary embodiments of the toothbrush, including, for example, exemplary embodiments other than those described in FIGS. 1-3.)

Still referring to exemplary FIGS. 1-3, the arm of the toothbrush may have a curvature of any angle. For example, in an exemplary embodiment, the arm may have a curvature of approximately 9 to 40 degrees from the body. In some exemplary embodiments, the curvature may be adjusted or may otherwise be made during the formation of the toothbrush so that it remains at a fixed angle. It may be appreciated, however, that the curvature of the arm may vary between toothbrushes, for example, depending on an application or depending on a user or a species or breed of animal with which the toothbrush may be used, each of which may require or which may be best facilitated by a slightly different angle of curvature of the arm. Further, the head and arm may be formed in any shape. For example, the head and arm may have a cylindrical, circular, or rounded shape so as to provide for comfort in use in a mouth.

In still further exemplary embodiments, and still referring to exemplary FIGS. 1-3, it may be appreciated that the body or handle may have any kind of cross-section, and may be flat, rectangular, square, cylindrical, or any combination thereof, as desired. Additionally, and with respect to any exemplary embodiment described herein, the toothbrush may be formed to be substantially detachable or capable of coupling to another device. For example, in some exemplary embodiments, the toothbrush may be a toothbrush head that could be coupled to a motorized handle. Alternatively, the toothbrush could be coupled to another toothbrush to form a double headed toothbrush, or the like.

Looking specifically at exemplary FIG. 1, FIG. 1 depicts a perspective image of an exemplary embodiment of a toothbrush 100. According to an exemplary embodiment, a toothbrush may have a handle 108 and a single brush head portion 102, which may have a plurality of bristles 104 protruding therefrom.

According to an exemplary embodiment, the handle 108 may have a generally circular cross-section having an ergonomic design for gripping and maneuvering the toothbrush 100. For example, according to an exemplary embodiment, the generally circular handle 108 may have an end portion 114 having a near-circular polygonal cross section, which may prevent the handle 108 from rotationally shifting in the hand of the user when gripped firmly by the user. The handle 108 may further have a gripping portion, which may be formed from a handle neck 112 which may terminate in a thicker handle node portion 110 disposed on the distal end of the handle 108. In an exemplary embodiment, the handle neck 112 may have a shallow taper along the length of the handle neck 112 beginning at the end portion 114 and terminating at the handle node 110. In some exemplary embodiments, the neck 112 may have a circular cross section, which may facilitate gripping of the handle 108 by the user and prevent the handle 108 from shifting in a proximal or distal direction parallel to the length of the handle 108 when gripped firmly by the user. In some exemplary embodiments, the handle node 110 may likewise have a circular cross section or may have a polygonal cross section, as may be desired.

According to an exemplary embodiment, a toothbrush arm 106 may extend from the handle 108 of the toothbrush 100 at the handle node 110, and may connect to the brush head 102. According to an exemplary embodiment, the arm 106 of the toothbrush 100 may extend in a straight distal direction away from the handle 108 or may extend from the handle 108 at an angle, such as may be desired. For example, it may be desirable to slightly offset the brush head 102 from the handle 108, and in such an exemplary embodiment the arm 106 may extend at a slight angle away from the handle 108.

According to an exemplary embodiment, the toothbrush arm 106 may terminate in a brush head 102, which may extend at an angle away from the toothbrush arm 106, for example at an angle of 9 to 40 degrees or any other angle as may be desired. (For example, a deeper angle, such as 50 degrees, or a shallower one, such as 5 degrees, may instead be selected. It may also be understood that the brush may have, in some exemplary embodiments, a gradual curve with no clearly-defined angle.)

A plurality of bristle tufts 104 may be disposed on the brush head 102, which may extend in a perpendicular direction away from the brush head 102, such that they are tilted with respect to the handle 108 and extend outward in a direction facing generally away from the handle 108. In some exemplary embodiments, this relative tilting of the brush head 102 may provide a configuration which naturally orients the bristles either towards the gum line of the human or animal on which the brush 100 is being used, or away from the gum line and toward the gingival regions of the teeth, which may be obstructed by braces of a human user or which may be difficult to access on an animal subject. According to an exemplary embodiment, bristle tufts 104 may be disposed in a single line, with each bristle being between 5 mm and 10 mm in length and each bristle tuft 104 being spaced 0.5 mm to 4 mm from the previous bristle tuft, such as may be desired.

Looking next at exemplary FIG. 2, FIG. 2 depicts a rear image of an exemplary embodiment of a toothbrush 100. As in FIG. 1, according to an exemplary embodiment, a toothbrush 100 may have a handle 108 and a single brush head portion 102. Handle 108 may have a generally circular cross-section (or any other shape of cross-section such as may be desired) and may have a handle neck 112 terminating in a node portion 110 which may improve the grip and control of a user of the toothbrush 100. The handle 108 may be connected to an arm 106, which may have a brush head 102.

Looking next at exemplary FIG. 3, FIG. 3 depicts a top down image of an exemplary embodiment of a toothbrush 100. As in FIGS. 1 and 2, according to an exemplary embodiment, a toothbrush 100 may have a handle 108 and a single brush head portion 102. Handle 108 may have a generally circular cross-section (or any other shape of cross-section such as may be desired) and may have a handle neck 112 terminating in a node portion 110 which may improve the grip and control of a user of the toothbrush 100. The handle 108 may be connected to an arm 106, which may have a brush head 102.

According to an exemplary embodiment, toothbrush 100 may have, disposed on the brush head 102, a plurality of bristle tufts 104 disposed in a single line, or may have another configuration of bristle tufts 104 such as may be desired. In an exemplary embodiment, a variable number of bristle tufts 104 may be provided. In another exemplary embodiment, the number of bristle tufts 104 in the brush head 102 may be extensible or reducible at the user's discretion, for example by replacing a brush head 102, if desired.

Referring now to FIGS. 4A-6, a double headed toothbrush may be shown. It may be appreciated that for each head of the toothbrush shown here, similar structure, geometry, and orientation as described above with respect to FIGS. 1-3 may apply. For example, a central body or handle of the double headed toothbrush may be substantially square, rectangular, cylindrical, or any combination thereof. The heads of the double headed toothbrush may be substantially cylindrical, circular, or rounded so as to provide comfort in use. The bristles on each head may be any length, for example about 5 mm to about 10 mm. Additionally, there may be any number of bristle tufts, for example 3 to 10 or more. Further, the two heads of the double headed toothbrush may be releasably coupled to each other or a handle, permanently affixed to each other or a handle or otherwise coupled. For example, a first head on a double headed toothbrush may be swapped out for a different head having a different arm angle or combination of arm angles. Such applications may be beneficial for use or treatment with different types of jaw structures or animals, replacing brush heads due to wear, or providing varied treatment to an intended user or animal. Additionally, one or both heads could be releasably attached and have couplings for mating one, both, or any other brush head to a motorized handle.

Figure 7:
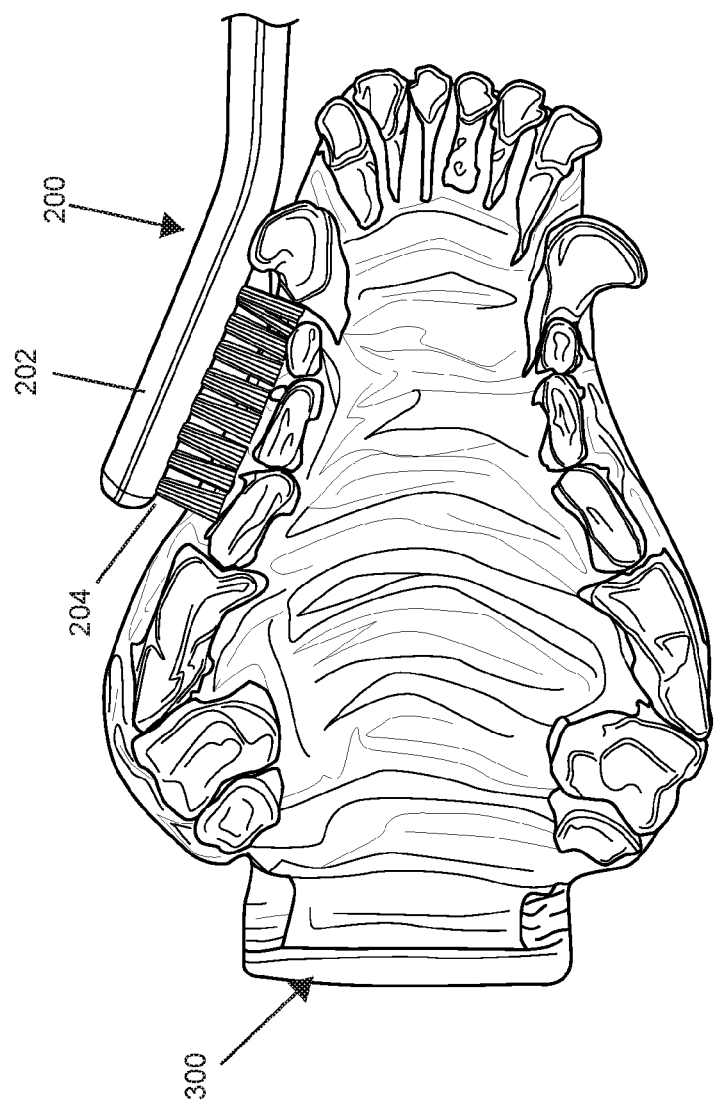
FIG. 7 is an exemplary image of a toothbrush in use.
Figure 8:
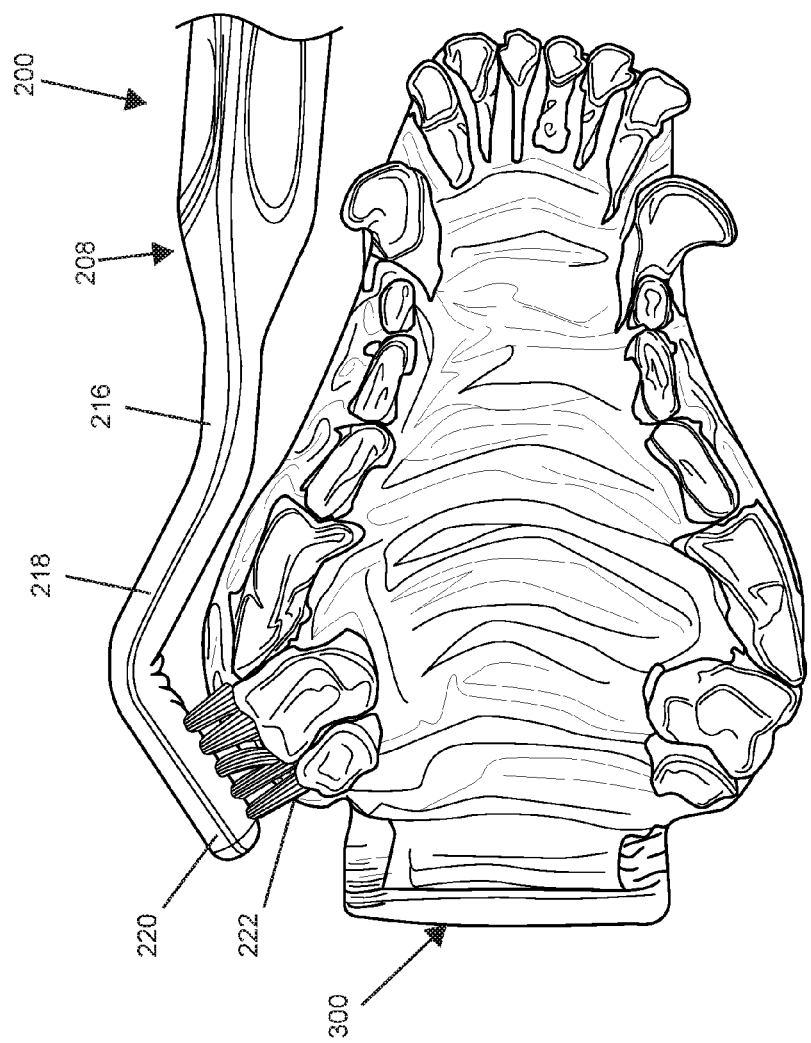
FIG. 8 is another exemplary image of a toothbrush in use.

Still referring to exemplary FIGS. 4A-6, a first head may have a head and arm with different bends or orientation with respect to the body or handle than a second head of the double headed toothbrush. On both ends of toothbrush body or gripping portion there may be arms which respectively connect to the brush heads. The arms may each extend away in the same direction from the longitudinal axis at an angle and thus laterally offset the brush heads from the gripping portion. The first brush head may extend from an arm, which in turn extends from the handle, at a desired angle; according to an exemplary embodiment, the brush head may extend from the arm at an angle of approximately 10 degrees, although any angle may be used; for example, according to an exemplary embodiment, the brush head may extend from the arm at an angle from about 9 degrees to about 50 degrees. The second brush head may have an arm having multiple different angles or bends disposed therein; for example, according to an exemplary embodiment, an arm of the second brush head may have a first departure angle from the handle of about 20 degrees to about 50 degrees, for example about 23 degrees and may then have a second bend of about 20 degrees to about 120 degrees, for example about 36 degrees to provide for enhanced utility in navigating the mouth of an intended user or animal. This can be further illustrated in exemplary FIGS. 7-8, showing a first brush head in use in FIG. 7 and a second brush head of a double headed toothbrush in use in FIG. 8. As demonstrated in these figures, the different head, arm, and handle orientations may allow for the cleaning of teeth on varying jaw structures that could not have previously been cleaned without significant irritation or general ineffectiveness in providing teeth cleaning on the intended user or animal. As shown in these exemplary figures, such varying head and arm designs can allow for the cleaning of teeth that were previously inaccessible or otherwise positioned in such a manner that known toothbrushes could not access properly for cleaning.

Figure 4A:
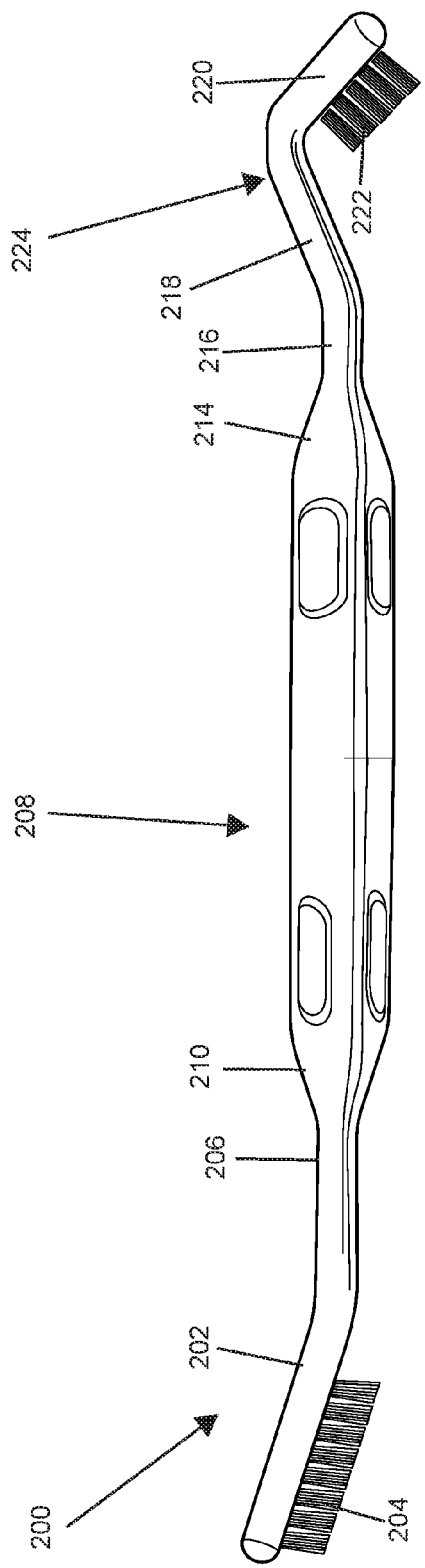
FIG. 4A is an exemplary image of a double headed toothbrush with varying arm contours.
Figure 4B:
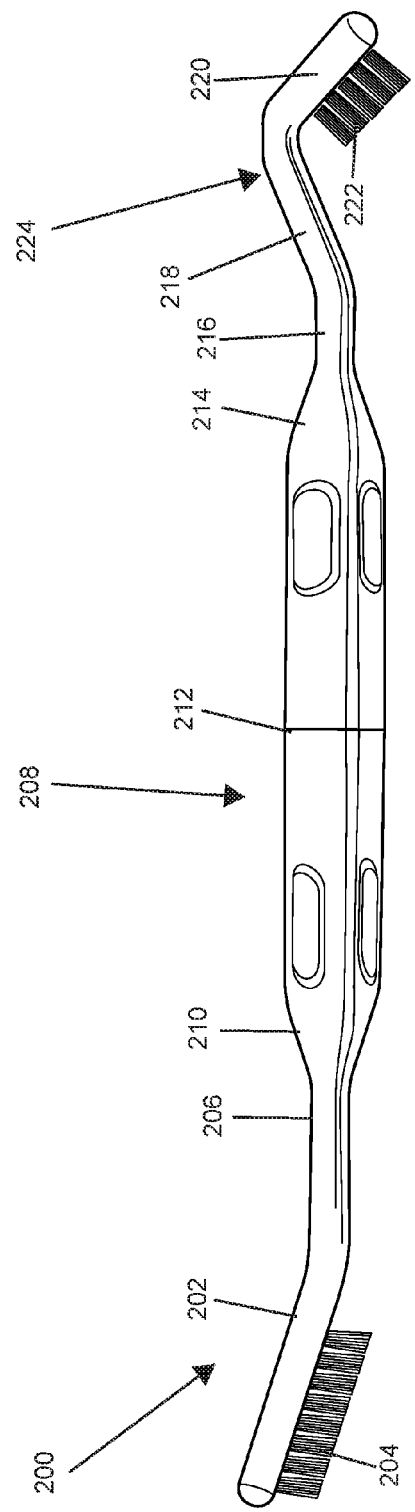
FIG. 4B is an exemplary image of a double headed toothbrush with varying arm contours.

Looking specifically at exemplary FIGS. 4A and 4B, FIGS. 4A and 4B depict an exemplary image of a double headed toothbrush 200 having varying arm contours. According to an exemplary embodiment, a double headed toothbrush 200 may have a first head 202 connected to a first arm 206 and having a plurality of bristle tufts 204 protruding therefrom, and may have a second head 220 having a plurality of bristle tufts 222 and may be connected to a second arm 224, which may have a plurality of intermediate portions or inter-bend portions 216, 218 bridging a plurality of bends.

According to an exemplary embodiment, the double headed toothbrush may further have a handle 208 disposed in the middle of the toothbrush 200 by which a user may be able to grip the toothbrush 200. According to an exemplary embodiment, the handle 208 may have a constant cross section, which may be polygonal (for example, square) or may be circular or another shape, as may be desired. In an exemplary embodiment, each end 210, 214 of the handle may taper from the handle cross section at a wider portion to the arms 206, 216 emerging from either side of the handle.

According to an exemplary embodiment, a first toothbrush arm 206 of the toothbrush 200 may extend in a straight distal direction away from the handle 208 or may extend from the handle 208 at an angle, such as may be desired. For example, it may be desirable to slightly offset the brush head 202 from the handle 208, and in such an exemplary embodiment the arm 206 may extend at a slight angle away from the handle 208. (In other exemplary embodiments, other shapes, such as a gradual curve with no clearly-defined angles, may also be understood.)

According to an exemplary embodiment, the first toothbrush arm 206 may terminate in a first brush head 202, which may extend at an angle away from the first toothbrush arm 206, for example at an angle of 9 to 50 degrees or any other angle as may be desired.

A plurality of bristle tufts 204 may be disposed on the first brush head 202, which may extend in a perpendicular direction away from the first brush head 202, such that they are tilted with respect to the handle 208 and extend outward in a direction facing generally away from the handle 208. In some exemplary embodiments, this relative tilting of the brush head 202 may provide a configuration which naturally orients the bristles either towards the gum line of the human or animal on which the brush 200 is being used, or away from the gum line and toward the gingival regions of the teeth, which may be obstructed by braces of a human user or which may be difficult to access on an animal subject. According to an exemplary embodiment, bristle tufts 204 may be disposed in a single line, with each bristle being between 5 mm and 10 mm in length and each bristle tuft 204 being spaced 0.5 mm to 4 mm from the previous bristle tuft, such as may be desired. In another exemplary embodiment, another configuration of bristle tufts 204 may be used, as may be desired.

According to an exemplary embodiment, a second toothbrush arm 224 may extend in a first direction away from the handle 208, which may be, for example, a straight proximal direction or at an angle, as may be desired. (In some exemplary embodiments, the second toothbrush arm 224 may also have another shape, such as, for example, a gradual curve having no clearly-defined angles.) The second toothbrush arm 224 may have a plurality of bends; for example, according to an exemplary embodiment, the second toothbrush arm 224 may have a first straight portion 216 extending in a straight proximal direction away from the handle 208, may have a first bent portion 218 extending away from the first straight portion 216 at an angle, and may have a second brush head 220 extending away from the first bent portion 218 at an angle, such that the bristle tufts 222 of the second brush head 220 face in an inward direction oriented toward the handle 208 of the toothbrush 200. (In some exemplary embodiments, it may be desired to separate the toothbrush arm 224 into multiple connected components, which may allow the use of a greater range of angles or shapes than may be possible if the toothbrush arm 224 was formed from one component. In some exemplary embodiments, toothbrush arms 224, particularly toothbrush arms 224 having an extreme angle, may be manufactured in such a fashion, if desired.)

According to an exemplary embodiment, each of the heads 202, 220 of the double-headed toothbrush 200 may be substantially cylindrical, circular, or rounded so as to provide comfort in use; in some exemplary embodiments, each head 202 may be the same shape or may be a different shape, as may be desired.

According to an exemplary embodiment, the bristle tufts 204, 222 on each of the brush heads 202, 220 may be of any length. For example, according to an exemplary embodiment, the bristles on each head may be about 5 mm to about 10 mm. The bristles on each head 202, 220 may be the same lengths or different lengths, such as may be desired.

In some exemplary embodiments, such as may be shown in FIG. 4B, each of the heads 202, 220 may be detachable from the handle 208, such that one head 202, 220 may be swapped out for another head 202, 220 such as may be desired. For example, according to an exemplary embodiment, the handle 208 may be formed from two pieces coupled together at a parting line 212, and the pieces may be screwed together or otherwise coupled together in order to form a handle 208. In some other exemplary embodiments, swapping of the heads may be done through another method, and may, for example, be done through coupling the first arm portion 206 to the handle 208 at a releasable coupling mounted at the end of the handle 210 such that the first arm portion 206 can be removed from the handle and replaced with another arm portion 206. Likewise, the other end 214 of the handle 208 may also be or may also have a releasable coupling, if desired.

In an exemplary embodiment in which the heads 202, 220 are detachable, each of the heads 202, 220 that may be fitted to the handle 208 may be designed with different bristle tip configurations in order to provide for optimal cleaning of teeth, such as teeth that have been fitted with orthodontic appliances or teeth of an animal. For example, according to an exemplary embodiment, a particular head 202, 220 may have between three and eight bristle tufts 204, 222 in a row, or may have a different number of tufts 204, 222, such as may be desired. In some exemplary embodiments, the replacement heads 202, 220 may be of different sizes, may extend at different angles, or may have different size arms from one another.

In another exemplary embodiment, the pieces may be rotationally adjusted relative to one another in order to change the relative adjustment of the brush heads 202, 220; this may give a user of the toothbrush 200 greater control over it and allow them to more readily switch between the first brush head 202 and the second brush head 220 in whatever manner may be most comfortable for them, or may allow them to use one of the two brush heads 202, 220 as a handle extension if additional handle length is found to be necessary, such as may be desired.

Figure 5:
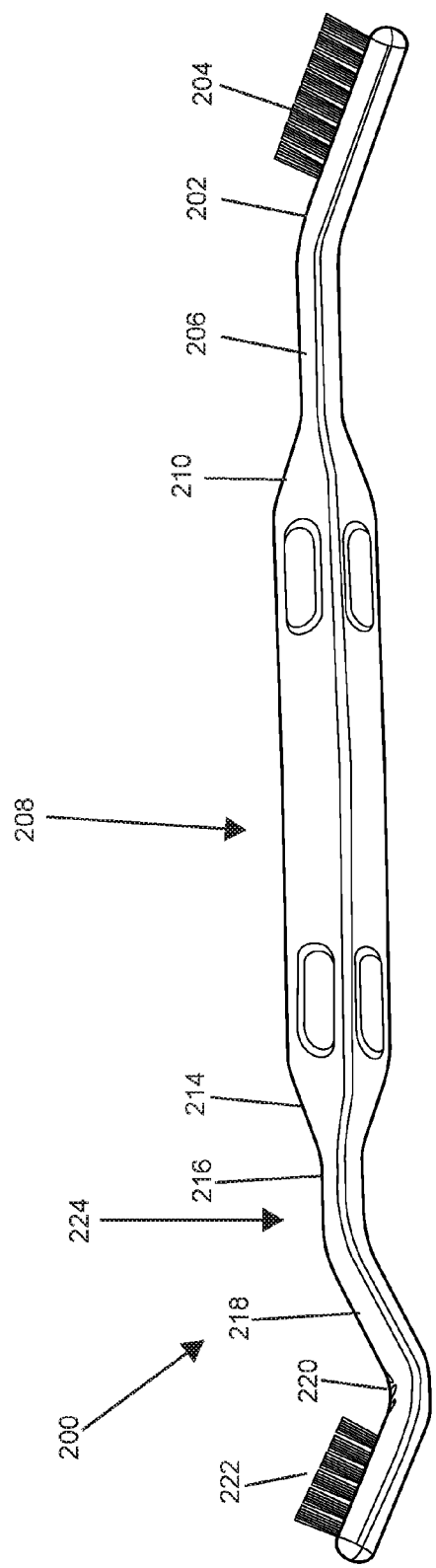
FIG. 5 is another exemplary image of a double headed toothbrush with varying arm contours.

Looking specifically at exemplary FIG. 5, FIG. 5 depicts another exemplary image of a double headed toothbrush 200 having varying arm contours. According to an exemplary embodiment, a double headed toothbrush 200 may have a first head 202 connected to a first arm 206 and having a plurality of bristle tufts 204 protruding therefrom, and may have a second head 220 having a plurality of bristle tufts 222 and may be connected to a second arm 224, which may have a plurality of inter-bend portions 216, 218.

Figure 6:
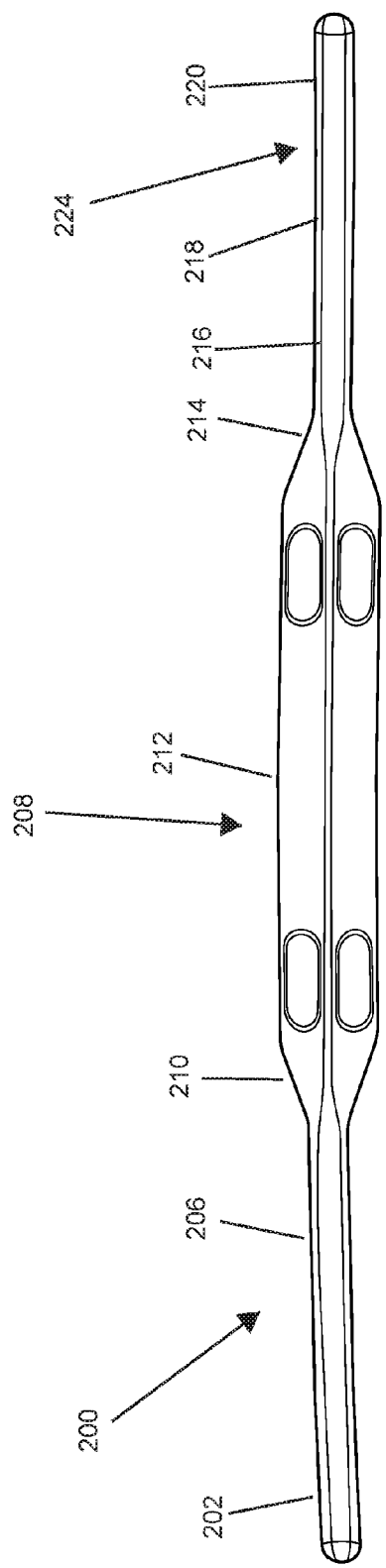
FIG. 6 is an exemplary center view of a double headed toothbrush.

Looking specifically at exemplary FIG. 6, FIG. 6 depicts an exemplary center view image of a double headed toothbrush 200 having varying arm contours. According to an exemplary embodiment, a double headed toothbrush 200 may have a first head 202 connected to a first arm 206, and may have a second head 220 connected to a second arm 224, which may have a plurality of inter-bend portions 216, 218.

Looking specifically at exemplary FIGS. 7 and 8, FIGS. 7 and 8 depict an exemplary image of a toothbrush 200 in use. Specifically, the toothbrush 200 may be shown in use on an animal skull. As shown in FIGS. 7 and 8, the angled configuration of the toothbrush 200, with the above configurations of the brush heads 202, 220 provides for the bristle tufts 204, 222 to easily reach and clean along the gumline and the gingival regions of the facial surfaces of teeth that may be obstructed by an unusual mouth shape or dentition structure 300. Therefore, dental plaque along the gumline, and/or food that may be lodged in the back teeth, of a pet cat or dog may be removed using an exemplary embodiment of the toothbrush 200 described herein. The same may be true for using the toothbrush in a human mouth where some of the teeth are obstructed by orthodontic braces.

Figure 9:
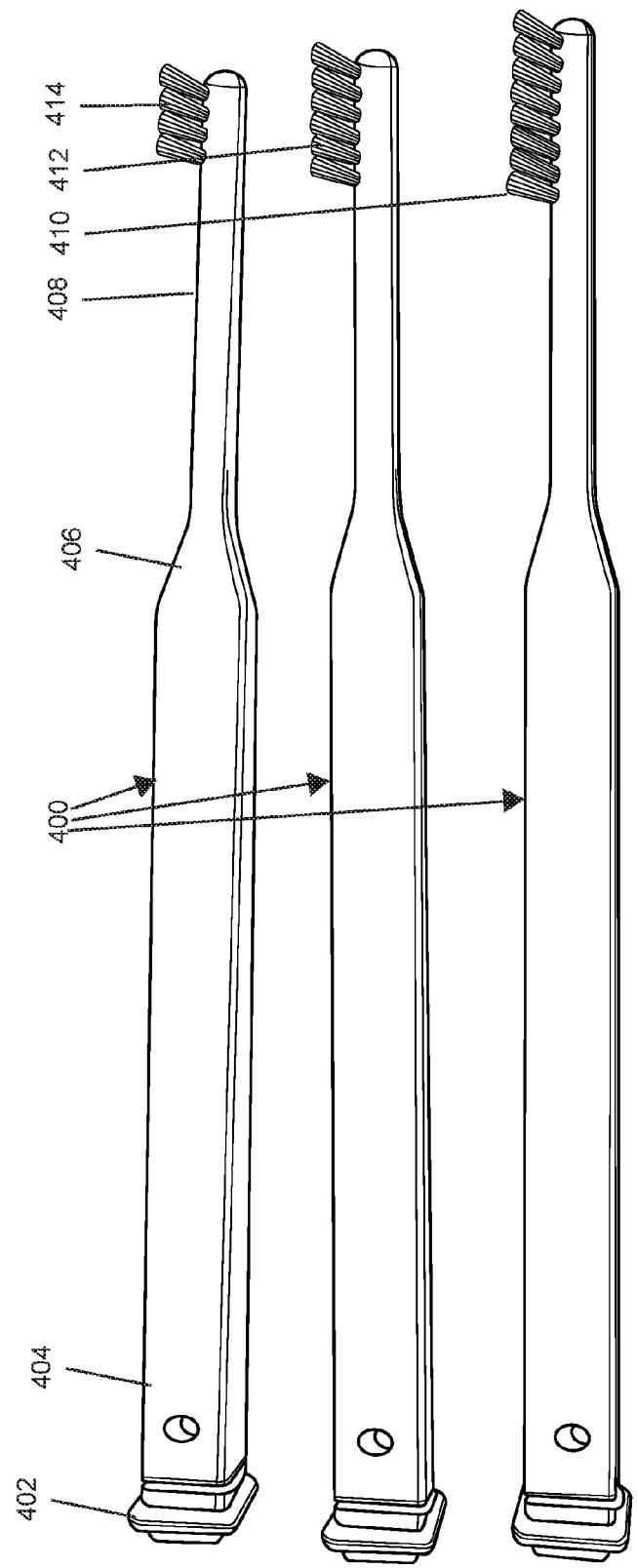
FIG. 9 is an exemplary image of various toothbrushes.

In still further exemplary embodiments, and referring now to exemplary FIG. 9, it may be appreciated that the toothbrush may have further orientations and components. As shown in exemplary FIG. 9, various toothbrushes with straight heads, arms, and handles, and between 4 and 8 bristle tufts are shown. These can be varied, as desired, according to the exemplary embodiments described herein.

For example, according to an exemplary embodiment, a toothbrush 400 may have a handle 404 having a square cross-section, having a distal end 406 which tapers into a toothbrush arm 408 supporting a head with a plurality of bristle tufts 410, 412, 414. According to an exemplary embodiment, a toothbrush head may be provided with a variable number of bristle tufts 410, 412, 414; for example, according to some exemplary embodiments, a first toothbrush head may be provided with four bristle tufts 414, a second toothbrush head may be provided with six bristle tufts 412, and a third toothbrush head may be provided with eight bristle tufts 410. Other numbers of bristle tufts may also be used, such as may be desired. In some exemplary embodiments, bristle tufts may be disposed so that they are arranged in a line, in parallel rows, or in staggered rows, such as may be desired.

According to an exemplary embodiment, a toothbrush 400 may have an end cap 402 which may in some exemplary embodiments be removable. According to an exemplary embodiment, an end cap 402 may cover a connector that may be used to connect a toothbrush 400 to another toothbrush 400, permitting the toothbrush 400 to be connected to another toothbrush to form a double-headed toothbrush 400 similar to those depicted in previous figures. In some exemplary embodiments, a connector hidden by an end cap 402 may be directly connected to a connector hidden by the end cap 402 of another toothbrush; in some other exemplary embodiments, an intermediate piece may be disposed between each half of the double-headed toothbrush 400. In some exemplary embodiments, it may be desired to have the handle 404 be hollow or partially hollow, for example in order to make the interior of the handle 404 functional as storage. For example, in some exemplary embodiments, the handle 404 may be used as storage for one or more other dental care items, such as, for example, a smaller toothbrush or one or more dental care chews; in other exemplary embodiments, the handle 404 may be used as storage for one or more other items, such as, for example, standard pet treats to be used as a reward after brushing, as may be desired.

Turning next to exemplary FIGS. 10 and 11, FIGS. 10 and 11 may depict an exemplary image of a double-headed toothbrush 500 having varying arm contours. According to an exemplary embodiment, the double headed toothbrush 500 may have a first head 502 connected to a first arm 506 and having a plurality of bristle tufts 504 protruding therefrom, and may have a second head 520 having a plurality of bristle tufts 522 and may be connected to a second arm 524, which may have a plurality of inter-bend portions 516, 518. The double-headed toothbrush may further have a handle 508 disposed in the middle of the toothbrush 500 by which a user may be able to grip the toothbrush 500.

According to an exemplary embodiment, the double-headed toothbrush 500 may have a first head 502 of the double-headed toothbrush 500 extending straight out from the first arm 506 of the double-headed toothbrush 500 along a first axis 526. In an exemplary embodiment, the first head 502 of the double-headed toothbrush 500 may be disposed at an angle, such as a first angle 528, from an axis 530 of the first arm 506 of the double-headed toothbrush 500.

According to an exemplary embodiment, each of the first arm 506, the handle 508, and the first bend of the second arm 516 may be disposed along a second axis 530 extending from the first arm 506 to the first bend of the second arm 516, such that each of these features is arranged linearly with one another. In another exemplary embodiment, one or more of the features may deviate from the second axis 530, if desired; for example, in an exemplary embodiment, the first arm 506 may be provided at a slight angle from the end 510 of the handle 508, or the second arm 516 may likewise be provided at an angle from the end 514 of the handle 508. (As in other exemplary embodiments, other shapes may also be contemplated, if desired; for example, according to an exemplary embodiment, the first arm 506 or the second arm 516 may have more or fewer angles than those shown, or may be provided at a gradual curve with no clearly defined angles, or may have another shape such as may be desired. For example, in some exemplary embodiments, it may be desired to provide an arm 506, 516 with bends in a first planar direction as well as a second planar direction, as may be desired. It may, for example, also be desired to have the same shape be used for different dispositions or orientations of the bristle tufts 504, 522; for example, in an exemplary embodiment, a brush head 502, 520 may be rotated at an angle of 45 degrees, 90 degrees, or another angle relative to the direction of bending of the toothbrush arm 506, 524, such that the angles 528, 532, 536 provided in the toothbrush arms are disposed in a first planar direction and such that the bristle tufts 504, 522 extend in a second planar direction. In some exemplary embodiments, more than one set of bristle tufts 504, 522 may be provided, or a wide arc of bristle tufts 504, 522 may be provided. In some exemplary embodiments, the orientation of a set of bristle tufts 504, 522 may be adjustable.)

According to an exemplary embodiment, the second bend in the second arm 518 may be provided at an angle 532 from the second axis 530, and may extend straight along a third axis 534. The head 520 of the second arm may be provided at an angle 536 from the third axis 534, and may extend straight along a fourth axis 538. In some exemplary embodiments, other configurations of the second arm 524, or even of the first arm 506, may also be provided; for example, in an exemplary embodiment, a second arm 524 may be curved in an S-shape or similar shape and may have no sections that extend straight along an axis, if desired.

In some exemplary embodiments, the first brush head 504 of the first toothbrush arm 506 may extend at an angle away from the first toothbrush arm 506 at an angle of approximately 9 to 50 degrees. As such, the outside angle 528 of the first toothbrush arm 506 may be 180 minus 9 to 50 degrees, or approximately 130 to 171 degrees. Likewise, the first of the outside angles 532 of the second brush arm may be in this range (that is, the first of the outside angles 532 of the second brush arm 524 may be 180 minus 9 to 50 degrees, or approximately 130 to 171 degrees). The second of the outside angles 536 of the second brush arm 524 may have a wider range of possible angle measurements; for example, in some exemplary embodiments, the second of the outside angles 536 may have a measurement of between 60 degrees and 160 degrees (or a range of 180 minus 20 degrees to 180 minus 120 degrees). In some exemplary embodiments, it may be desired to have a second outside angle 536 of the second arm 524 be approximately 36 degrees, so that the bristle tufts 522 of the second arm 524 can be oriented in a direction more favorable for brushing the back teeth of an animal. Other angle measurements can be used for any of the angles of the toothbrush 500 such as may be desired.

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A toothbrush for cleaning gums and teeth in the mouth of a human or animal, comprising:
   a handle having a proximal end and a distal end;
   a first arm disposed on the proximal end of the handle and a second arm disposed on the distal end of the handle, each arm being coplanar with a longitudinal plane of the handle, each arm extending outward from the handle in an initial direction collinear with a longitudinal axis of the handle;

wherein the second arm comprises at least one bent portion, the at least one bent portion of the second arm extending laterally in a first lateral direction from the longitudinal axis of the handle at a second arm first angle;

a first brush head and a second brush head, each brush head being coplanar with the longitudinal plane of the handle, the first brush head extending laterally from the longitudinal axis of the handle at a first arm angle and the second brush head extending laterally from the at least one bent portion of the second arm at a second angle different from the first arm angle, wherein the second brush head extends in a second lateral direction opposite the first lateral direction; and at least one bristle tuft extending laterally from each of the first brush head and the second brush head, each bristle tuft being oriented perpendicular to a longitudinal axis of the brush head.

2. The toothbrush of claim 1, wherein the first arm angle is an angle between 9 and 50 degrees.

3. The toothbrush of claim 2, wherein the first arm angle is 10 degrees.

4. The toothbrush of claim 1, wherein the second arm first angle is an angle between 20 and 50 degrees.

5. The toothbrush of claim 4, wherein the second arm first angle is 23 degrees.

6. The toothbrush of claim 1, wherein the second arm second angle is an angle between 20 and 120 degrees.

7. The toothbrush of claim 6, wherein the second arm second angle is 36 degrees.

8. The toothbrush of claim 6, wherein the angle between the longitudinal axis of the second brush head and the longitudinal axis of the handle is an oblique angle.

9. The toothbrush of claim 1, wherein the at least one bristle tuft of the first brush head and the at least one bristle tuft of the second brush head each extend in the second lateral direction.

10. The toothbrush of claim 1, wherein the handle comprises a polygonal cross-section and is linear, wherein each of the first arm, the second arm, the first brush head, and the second brush head comprises a cylindrical shape with a circular cross-section, each of the first brush head and the second brush head having a dome-shaped end; and wherein the handle has a thickness greater than the thickness of the first arm and the second arm, and wherein the proximal end and the distal end of the handle taper from the handle to the first arm and the second arm.

11. The toothbrush of claim 1, wherein each of the at least one bristle tufts extends between 5 and 10 mm from the brush head.

12. The toothbrush of claim 11, wherein each of the at least one bristle tufts extends 8 mm from the brush head.

13. The toothbrush of claim 1, wherein each of the first brush head and the second brush head has a plurality of bristle tufts, each plurality of bristle tufts arranged in a single line on each brush head.

14. The toothbrush of claim 1, wherein the handle comprises a proximal end piece and a distal end piece, each of the proximal end piece and the distal end piece having a connector, wherein the proximal end piece and the distal end piece are mated at each connector.

15. The toothbrush of claim 14, wherein the proximal end piece and the distal end piece are rotationally adjustable with respect to one another, and wherein the rotational adjustment of the proximal end piece and the distal end piece with respect to one another effects an adjustment of a relative orientation of the brush heads.

16. A toothbrush for cleaning gums and teeth in the mouth of a human or animal, comprising:

a handle having a proximal end and a distal end;

an arm disposed on the distal end of the handle, said arm having a cylindrical shape and substantially circular cross section, the arm being coplanar with a longitudinal plane of the handle, the arm extending outward from the handle in an initial direction collinear with a longitudinal axis of the handle;

a brush head, the brush head being coplanar with the longitudinal plane of the handle, the brush head extending laterally from the longitudinal axis of the handle at an angle in a first lateral direction, said brush head having a substantially circular cross-section and a substantially dome-shaped end;

a plurality of bristle tufts extending laterally from the brush head, the plurality of bristle tufts being oriented perpendicular to a longitudinal axis of the brush head, the plurality of bristle tufts comprising a plurality of bristles having a length of between 5 mm and 10 mm and extending from the brush head in a common direction and parallel with each other; and a connector disposed on the proximal end of the handle, the connector configured to couple the toothbrush to a second toothbrush to form a double-ended toothbrush.

17. The toothbrush of claim 16, wherein the brush head extends laterally from the longitudinal axis of the handle at a brush head angle, and wherein the brush head angle is an angle between 9 and 50 degrees.

18. The toothbrush of claim 16, wherein the arm has at least one bent portion, the at least one bent portion of the arm extending laterally in a first lateral direction from the longitudinal axis of the handle at an arm angle, the brush head extending in a second lateral direction opposite the first lateral direction at a brush head angle;

wherein the arm angle is an angle between 20 and 50 degrees; and wherein the brush head angle is an angle between 20 and 120 degrees.

19. The toothbrush of claim 16, wherein the handle comprises a polygonal cross-section and is linear, wherein the arm and the brush head each comprise a cylindrical shape with a circular cross-section, the brush head having a dome-shaped end; and wherein the handle has a thickness greater than the thickness of the arm, and wherein the proximal end of the handle tapers from the handle to the arm.

20. The toothbrush of claim 16, wherein the connector is configured to rotationally couple the toothbrush to a second toothbrush.

* * * * *